United States Patent
Rigg et al.

(10) Patent No.: US 11,253,448 B2
(45) Date of Patent: Feb. 22, 2022

(54) INORGANIC SUNSCREEN AGENTS WITH HIGHER UV RADIATION PROTECTION

(71) Applicant: VIZOR, LLC, Middlesex, NJ (US)

(72) Inventors: Yannick Rigg, Springfield Gardens, NY (US); Richard Rigg, Richmond Hills, NY (US)

(73) Assignee: VIZOR, LLC, Middlesex, NJ (US)

( * ) Notice: Subject to any disclaimer, the term of this patent is extended or adjusted under 35 U.S.C. 154(b) by 0 days.

(21) Appl. No.: 16/638,165

(22) PCT Filed: Aug. 31, 2018

(86) PCT No.: PCT/US2018/049027
§ 371 (c)(1),
(2) Date: Feb. 11, 2020

(87) PCT Pub. No.: WO2019/050785
PCT Pub. Date: Mar. 14, 2019

(65) Prior Publication Data
US 2020/0188248 A1 Jun. 18, 2020

Related U.S. Application Data

(60) Provisional application No. 62/554,060, filed on Sep. 5, 2017.

(51) Int. Cl.
| | | |
|---|---|---|
| *A61K 8/27* | (2006.01) | |
| *A61K 8/02* | (2006.01) | |
| *A61K 8/06* | (2006.01) | |
| *A61K 8/29* | (2006.01) | |
| *A61K 8/35* | (2006.01) | |
| *A61K 8/365* | (2006.01) | |
| *A61Q 17/04* | (2006.01) | |

(52) U.S. Cl.
CPC .............. *A61K 8/27* (2013.01); *A61K 8/0241* (2013.01); *A61K 8/062* (2013.01); *A61K 8/064* (2013.01); *A61K 8/29* (2013.01); *A61K 8/35* (2013.01); *A61K 8/365* (2013.01); *A61Q 17/04* (2013.01); *A61K 2800/412* (2013.01); *A61K 2800/413* (2013.01); *A61K 2800/622* (2013.01); *A61K 2800/651* (2013.01)

(58) Field of Classification Search
CPC ........ A61K 8/27; A61K 8/0241; A61K 8/062; A61K 8/064; A61K 8/29; A61K 8/35; A61K 8/365; A61K 2800/412; A61K 2800/413; A61K 2800/622; A61K 2800/651; A61K 2800/624; A61K 8/85; A61Q 17/04
See application file for complete search history.

(56) References Cited

U.S. PATENT DOCUMENTS

| | | |
|---|---|---|
| 2006/0264552 A1 | 11/2006 | Frerichs |
| 2007/0218021 A1 | 9/2007 | Wells |
| 2008/0299057 A1 | 12/2008 | Lin |
| 2011/0097288 A1* | 4/2011 | Janssen .................... A61K 8/06 424/60 |
| 2011/0150792 A1* | 6/2011 | Shao .................... A61K 8/0241 424/59 |

FOREIGN PATENT DOCUMENTS

| | | |
|---|---|---|
| JP | 2012-521442 A | 9/2012 |
| WO | WO 2010/091963 | 8/2010 |
| WO | WO 2010/111279 A1 | 9/2010 |
| WO | WO 2016/183209 | 11/2016 |
| WO | WO 2017/083118 | 5/2017 |

OTHER PUBLICATIONS

PCT/US2018/049027, International Search Report and Written Opinion dated Dec. 20, 2018, 7 pages—English.
Shi Yu, Carboxyl group (-CO2H) functional ferromagnetic iron oxide nanoparticles for potential bio-applications, *J. Mater. Chem.* 2004, 14, 2781-2786, Issue 18, Sep. 2004, Pubs.rsc.org/en/content/articlelanding/2004.
JP 2020-514249, Notice of Reasons for Rejection dated May 11, 2021, 3 pages—Japanese; 6 pages—English.
EP 18854507.3, Extended European Search Report dated Apr. 27, 2021, 8 pages—English.

* cited by examiner

*Primary Examiner* — Quanglong N Truong
(74) *Attorney, Agent, or Firm* — Andrew F. Young; Nolte Lackenbach Siegel

(57) ABSTRACT

Ultraviolet radiation sun protective compositions are reported which feature micronized metal oxide inorganic particles selected from zinc oxide, titanium oxide and mixtures thereof, the inorganic particles being coated with poly [$C_8$-$C_{20}$ hydroxycarboxylic acid], the coated particles measured at a 10% loading in dodecane and 1 minute elapsed time having a Zeta Potential ranging from 2 to 10 mv, amounts of the poly [$C_8$-$C_{20}$ hydroxycarboxylic acid] to the inorganic particles being in a relative weight ratio of 1:100 to 1:10.

15 Claims, No Drawings

INORGANIC SUNSCREEN AGENTS WITH HIGHER UV RADIATION PROTECTION

CROSS REFERENCE TO RELATED APPLICATIONS

This application relates to, and claims priority from, WIPO Ser. No. PCT/US2018/049027 filed Aug. 31, 2018, the entire contents of which are incorporated herein by reference, which in turn claims priority from U.S. Ser. No. 62/554,060 filed Sep. 5, 2017, the entire contents of which are incorporated herein by reference.

FIGURE SELECTED FOR PUBLICATION

None

BACKGROUND OF THE INVENTION

Field of the Invention

The invention relates to inorganic metal oxide particles useful as sunscreen agent components for skin and personal care compositions.

Description of the Related Art

Sunlight can be seriously damaging to human skin and destructive to hair. Ultraviolet segments of sunlight are known to accelerate photo aging of the human dermis. Acute exposure may even cause painful erythema. For these reasons, cosmetic chemists often combine organic sunscreen agents into their formulations. The spectrum of UVA and UVB radiation ordinarily is addressed by cocktails of two or more organic sunscreen agents.

Unfortunately, organic type sunscreen agents suffer from certain problems. Under the bombardment of ultraviolet radiation, the organic sunscreens themselves degrade. Photostability may last for only a few hours. Consumers thinking that they are fully protected with their sunscreen lotion, often expose themselves for a time beyond the photostability limit. A second problem is that prominent organic sunscreen agents under certain conditions are prone to cause skin irritation.

In recent times, microfine zinc oxide and microfine titanium oxide have been shown to deflect ultraviolet radiation of both UVA and UVB type. No longer is photostability and skin irritation a problem. But with any new technology, issues do arise. One problem is formulation space. There is a limit to how much metal oxide particles can be suspended within a sunscreen or personal care composition. Ways are needed to raise the sun protective factor (SPF) while keeping constant the level of metal oxide particles.

Background literature includes the following disclosures. U.S. Pat. No. 5,587,148 (Mitchell and Mitchnik) discloses as sunscreen agent a dispersion of micronized particles of zinc oxide with diameter of less than 0.2 micron (200 nm).

U.S. Pat. No. 8,623,386 B2 (Schlossman et al.) describes coated metal oxide particles used as pigments in cosmetic compositions. These particles are reported available in primary particle size less than 200 nm and also as pigmentary grade with sizes larger than 200 nm. Coatings are preferably jojoba ester but may also be selected from soya wax, candililla wax, castor oil, coconut oil, macadamia nut oil, and even many fractions of mineral oil.

U.S. Pat. No. 9,254,398 (Schlossman et al.) discloses a series of two-layer coated micronized metal oxide powders with good self-dispersibility. These are intended as ingredients for cosmetic products such as makeup, lipstick, nail enamel, eye shadow and mascara. The first of the two layers is triethoxycaprylylsilane. The second, an outer coating, is polyhydroxystearic acid.

Commercial dispersing agents for sunscreens under the trademark DISPERSUN are marketed by Innospec Inc. The company in a product brochure (Issue No. 4/2010) promotes use of DISPERSUN DSP-OL100 and DSP-OL300 (both identified as polyhydroxystearic acid) for dispersing ultrafine titanium dioxide and zinc oxide into sun protection cosmetic products. Higher sun protection factor (SPF) sunscreen was said to be achievable without increasing pigment levels. There is room for more improvement.

ASPECTS AND SUMMARY OF THE INVENTION

Ultraviolet radiation sun protective compositions are reported which feature micronized metal oxide inorganic particles selected from the group consisting of zinc oxide, titanium oxide and mixtures thereof, the inorganic particles being coated with a poly[$C_8$-$C_{20}$ hydroxycarboxylic acid], the coated particles measured at a 10% loading in dodecane and at 1 minute elapsed time having a Zeta Potential ranging from 2 to 10 mv, particularly from 2 to 5 mv, amounts of the poly[$C_8$-$C_{20}$ hydroxycarboxylic acid] to the inorganic particles being in a relative weight ratio of 1:100 to 1:10.

Advantageously in certain embodiments, the coated particles may be characterized when dispersed in tricaprylin at a 1:1 weight ratio as having a Brookfield Viscosity measured at 23-28° C., 20 rpm and spindle 4, ranging from 20 to 200 cps.

Further provided are cosmetic products based upon:
(i) ultraviolet radiation sun protective compositions including micronized metal oxide inorganic particles selected from the group consisting of zinc oxide, titanium oxide and mixtures thereof, the inorganic particles being coated with poly[$C_8$-$C_{20}$ hydroxycarboxylic acid], the coated particles measured at a 10% loading in dodecane and 1 minute elapsed time having a Zeta Potential ranging from 2 to 10 mv, especially from 2 to 5 mv, amounts of the poly[$C_8$-$C_{20}$ hydroxycarboxylic acid] to the inorganic particles being in a relative weight ratio of 1:100 to 1:10; and
(ii) a dermatologically acceptable carrier supporting the ultraviolet radiation sun protective compositions, the compositions being present in the carrier in a relative weight ratio of 1:100 to 1:4.

Still further provided is a method for producing ultraviolet radiation protective compositions which include the steps of:
i. providing in powdered form micronized metal oxide inorganic particles selected from the group consisting of zinc oxide, titanium dioxide and mixtures thereof;
ii. combining in a vessel non-oil slurried poly[$C_8$-$C_{20}$ hydroxycarboxylic acid] with the powdered form of the metal oxide inorganic particles to create coated particles surrounded with poly[$C_8$-$C_{20}$ hydroxycarboxylic acid], the coated particles measured at a 10% loading in dodecane and 1 minute elapsed time having a Zeta Potential ranging from 2 to 10 mv, especially from 2 to 5 mv, amounts of the poly[$C_8$-$C_{20}$ hydroxycarboxylic acid] to the inorganic particles being in a relative weight ratio of 1:100 to 1:10; and
iii. discharging the coated particles from the vessel.

According to one aspect of the present invention, there is provided an ultraviolet radiation sun protective composition, comprising: micronized metal oxide inorganic particles selected from the group consisting of zinc oxide, titanium oxide and mixtures thereof, the inorganic particles being coated with poly[$C_8$-$C_{20}$ hydroxycarboxylic acid], the coated particles measured at a 10% loading in dodecane and 1 minute elapsed time having a Zeta Potential ranging from 2 to 10 mv, amounts of the poly[$C_8$-$C_{20}$ hydroxycarboxylic acid] to the inorganic particles being in a relative weight ratio of 1:100 to 1:10, including every ratio between this range at intervals of 05; for example 1:95, 1:90, . . . to . . . 1:6, 1.55, 1:50.

According to another alternative aspect of the present invention, there is provided an ultraviolet radiation sun protective composition, wherein: the Zeta Potential ranges from 2 to 5 mv, including but not limited to 2, 2.5, 3, 3.5, 4, 4.5 and 5 mv.

According to another alternative aspect of the present invention, there is provided a an ultraviolet radiation sun protective composition, wherein the coated particles are characterized when dispersed in tricaprylin at a 1:1 weight ratio as having a Brookfield Viscosity measured at 23-28° C., 20 rpm with spindle 4, ranging from 20 to 200 cps.

According to another alternative aspect of the present invention, there is provided an ultraviolet radiation sun protective composition, wherein the poly[$C_8$-$C_{20}$ hydroxycarboxylic acid] is selected from the group consisting of polyhydroxystearic acid, polyricinoleic acid and mixtures thereof.

According to another alternative aspect of the present invention, there is provided an ultraviolet radiation sun protective composition, wherein the poly[$C_8$-$C_{20}$ hydroxycarboxlic acid] is polyhydroxystearic acid.

According to another alternative aspect of the present invention, there is provided an ultraviolet radiation sun protective composition, being free of oily dispersant.

According to another alternative aspect of the present invention, there is provided an ultraviolet radiation sun protective composition, wherein the composition is formed in an oily dispersant free process selected from the group consisting of (1) high speed milling, (2) supercritical carbon dioxide processing and (3) solvent slurry application with subsequent solvent removal.

According to another alternative aspect of the present invention, there is provided an ultraviolet radiation sun protective composition, wherein the poly[$C_8$-$C_{20}$ hydroxycarboxylic acid] to inorganic particles are in a relative weight ratio of 1:50 to 1:20, including but not limited to 1:50, 1:45, 1:40, 1:35, 1:30, 1:25, and 1:20.

According to another alternative aspect of the present invention, there is provided an ultraviolet radiation sun protective composition, wherein the inorganic particles have primary particle size ranging from 5 to 500 nm, including but not limited to every size between 5-to-500 nm at intervals of 0.5 mn; for example 5.5 nm, 6.0, 6.5, 7.0, 7.5, 8.0 . . . to 499, 499.5, and 500 nm.

According to another alternative aspect of the present invention, there is provided a cosmetic product, comprising: (i) ultraviolet radiation sun protective compositions comprising micronized metal oxide inorganic particles selected from the group consisting of zinc oxide, titanium oxide and mixtures thereof, the inorganic particles being coated with poly[$C_8$-$C_{20}$ hydroxycarboxylic acid], the coated particles measured at a 10% loading in dodecane and 1 minute elapsed time having a Zeta Potential ranging from 2 to 10 mv, amounts of the poly[$C_8$-$C_{20}$ hydroxycarboxylic acid] to the inorganic particles being in a relative weight ratio of 1:100 to 1:10; and (ii) a dermatologically acceptable carrier supporting the ultraviolet radiation sun protective compositions, the compositions being present in the carrier in a relative weight ratio of 1:100 to 1:50, including every ratio between this range at intervals of 05; for example 1:95, 1:90, . . . to . . . 1:6, 1.55, 1:50.

According to another alternative aspect of the present invention, there is provided a cosmetic product, wherein: the carrier is selected from the group consisting of water, emollients, fatty acids, fatty alcohols, humectants, thickeners and mixtures thereof.

According to another alternative aspect of the present invention, there is provided a cosmetic product, wherein: the coated ultraviolet sun protective compositions to the carrier are present in a relative weight ratio of 1:100 to 1:10, including every ratio between this range at intervals of 05; for example 1:95, 1:90, . . . to . . . 1:15, 1.10.

According to another alternative aspect of the present invention, there is provided a cosmetic product, wherein: the carrier is present in an amount from 1 to 99.9% by weight of the cosmetic product.

According to another alternative aspect of the present invention, there is provided a cosmetic product, further comprising: organic sunscreens selected from the group consisting of 2-ethylhexyl p-methoxycinnamate, 4,4'-t-butyl methoxydibenzoylmethane, octylsalicylate, tetraphthalylidene dicamphor sulfonic acid, benzophenone-3 and mixtures thereof.

According to another alternative aspect of the present invention, there is provided a composition, wherein the poly[$C_8$-$C_{20}$ hydroxycarboxylic acid] is selected from the group consisting of polyhydroxystearic acid, polyricinoleic acid and mixtures thereof.

According to another alternative aspect of the present invention, there is provided a composition, wherein the poly[$C_8$-$C_{20}$ hydroxycarboxlic acid] is polyhydroxystearic acid.

According to another alternative aspect of the present invention, there is provided a method for producing ultraviolet radiation protective compositions, comprising the steps of: (i) providing in powdered form micronized metal oxide inorganic particles selected from the group consisting of zinc oxide, titanium dioxide and mixtures thereof; (ii) combining in a vessel non-oil slurried poly[$C_8$-$C_{20}$ hydroxycarboxylic acid] with the powdered form of the metal oxide inorganic particles to create coated particles of inorganic particles surrounded with poly[$C_8$-$C_{20}$ hydroxycarboxylic acid], the coated particles measured at a 10% loading in dodecane and 1 minute elapsed time having a Zeta Potential ranging from 2 to 10 mv, amounts of the poly[$C_8$-$C_{20}$ hydroxycarboxylic acid] to the inorganic particles being in a relative weight ratio of 1:100 to 1:10; and (iii) discharging the coated particles from the vessel.

According to another alternative aspect of the present invention, there is provided a method for producing ultraviolet radiation protective compositions, wherein: the poly [$C_8$-$C_{20}$ hydroxycarboxylic acid] is selected from the group consisting of polyhydroxystearic acid, polyricinoleic acid and mixtures thereof.

According to another alternative aspect of the present invention, there is provided a method for producing ultraviolet radiation protective compositions, wherein: the poly [$C_8$-$C_{20}$ hydroxycarboxlic acid] is polyhydroxystearic acid.

According to another alternative aspect of the present invention, there is provided a method for producing ultraviolet radiation protective compositions, wherein: the coated particles are characterized such that when dispersed in tricaprylin at a 1:1 weight ratio as having a Brookfield Viscosity measured at 23-28° C., 20 rpm with spindle 4, ranging from 20 to 200 cps, and at any cps within that range.

The above and other aspects, features and advantages of the present invention will become apparent from the following description read in conjunction with the accompanying drawings, in which like reference numerals designate the same elements.

BRIEF DESCRIPTION OF THE DRAWINGS

None

DETAILED DESCRIPTION OF THE INVENTION

We have found that the SPF of micronized metal oxide inorganic particles can be improved by oil dispersant-free coating of the metal oxide particles with poly[$C_8$-$C_{20}$ hydroxycarboxylic acid], hereinafter also referred to as PHA. Effective oil dispersant-free coating methods include (1) high speed milling, (2) liquid carbon dioxide and supercritical carbon dioxide processing and (3) solvent slurry application with subsequent solvent removal. All three methods provided coated particles with SPF values approximately double those achieved with the known oil dispersant poly[$C_8$-$C_{20}$ hydroxycarboxylic acid] coating technique.

Relative weight ratio of the poly[$C_8$-$C_{20}$ hydroxycarboxylic acid] coating to the metal oxide may range from 1:100 to 1:10, especially from 1:50 to 1:20, more especially from 1:30 to 1:25 by weight. When placed within a cosmetic product having a carrier, the relative weight ratio of the coated ultraviolet radiation sun protective compositions to the carrier may range from 1:100 to 1:4, especially from 1:50 to 1:1.5.

Viscosities of the coated particles were measured in context of a 1:1 weight ratio slurry in Tricaprylin. The Tricaprylin is a glycerol trioctanoate available from Axona Inc. under the trademark Axona®, from Sigma-Aldrich division of Merck AG, and from Abitec Inc. IUPAC name is 2,3-di(octanoyloxy)propyl octanoate. Viscosities were taken using a Brookfield Viscometer DV-E with spindle number 4 at 23-28° C. The viscosities range from 20 to 200 cps, and particularly from 50 to 150 cps.

Advantageously the coated particles can be dosed to cosmetic product formulations in a fluid transport medium. Suitable media include triglyceride oils, hydrocarbons, silicones, fatty acids, fatty alcohols and combinations thereof. Especially useful as a fluid transport medium is Tricaprylin. When a fluid transport medium is used, the weight ratio relative to the coated particles may range from 5:1 to 1:5, especially from 2:1 to 1:2, and most especially about 1:1.

Metal Oxide Inorganic Particles

Micronized zinc oxide, titanium oxide and mixtures thereof are the most suitable metal oxides. The term 'micronized' means metal oxides having a primary particles size ranging from 5 to 500 nm, especially from 10 to 300 nm, when the particles are spherical or granular or amorphous. If the particles are acicular, the primary particle size may range from 5 to 50 nm by 50 to 150 nm. Primary particle size may be analyzed using Transmission Electron Microscopy.

Poly[$C_8$-$C_{20}$ Hydroxycarboxylic Acid]

Poly[$C_5$-$C_{20}$ hydroxycarboxylic acid] are oligomers of hydroxy fatty acids. Representative oligomers are polyhydroxystearic acid (PHSA), polyricinoleic acid and mixtures thereof. Polyhydroxystearic acids are oligomers of 12-hydroxystearic acid. These form by homopolymeric condensation of 12-hydroxystearic acid monomer units. The oligomer may have from 2 to 10, preferably from 2 to 4 repeating monomer units. The material is available from Innospec Inc.

In most instances, the poly[$C_8$-$C_{20}$ hydroxycarboxylic acid] will be the one and only coating surrounding the micronized metal oxide particles. Normally, no other substance will intervene between the poly[$C_8$-$C_{20}$ hydroxycarboxylic acid] coating and the micronized metal oxide particles.

Cosmetic Products

Cosmetic products formulated with the improved coated metal oxide sun protective particles usually include a dermatologically acceptable carrier. Amounts of the carrier may range from 1 to 99.9%, preferably from 60 to 95%, optimally from 70 to 90% by weight of the product. Among the useful carriers are water, emollients, fatty acids, fatty alcohols, humectants, thickeners and combinations thereof. The carrier may be aqueous, anhydrous or an emulsion. Preferably the compositions are aqueous, especially water and oil emulsions of the W/O or O/W or triplex W/O/W variety. Water when present may be in amounts ranging from 5 to 98%, preferably 20 to 70%, optimally from 35 to 60% by weight.

Water when present as carrier or otherwise may advantageously be incorporated into the compositions as a deionized, sterilized or pasteurized liquid or can be heat treated or irradiated after having been mixed with other components of the composition. These treatments insure elimination of pathogenic microbes.

Emollient materials may serve as dermatologically acceptable carriers. These may be in the form of silicone oils, synthetic or natural esters and hydrocarbons. Amounts of the emollients may range anywhere from 0.1 to 95%, preferably between 1 and 50% by weight of the cosmetic product.

Silicone oils may be divided into the volatile and nonvolatile variety. The term "volatile" as used herein refers to those materials which have a measurable vapor pressure at ambient temperature. Volatile silicone oils are preferably chosen from cyclic (cyclomethicone) or linear polydimethylsiloxanes containing from 3 to 9, preferably from 4 to 5, silicon atoms.

Nonvolatile silicone oils useful as an emollient material include polyalkyl siloxanes, polyalkylaryl siloxanes and polyether siloxane copolymers. The essentially nonvolatile polyalkyl siloxanes useful herein include, for example, polydimethyl siloxanes with viscosities of from about $5 \times 10^{-6}$ to 0.1 m$^2$/s at 25° C. Among the preferred nonvolatile emollients useful in the present compositions are the polydimethyl siloxanes having viscosities from about $1 \times 10^{-5}$ to about $4 \times 10^{-4}$ m$^2$/s at 25° C.

Another class of nonvolatile silicones are emulsifying and non-emulsifying silicone elastomers. Representative of this category is Dimethicone/Vinyl Dimethicone Crosspolymer available as Dow Corning 9040, General Electric SFE 839, and Shin-Etsu KSG-18. Silicone waxes such as Silwax WS-L (Dimethicone Copolyol Laurate) may also be useful.

Among the ester emollients are:

1) Alkyl esters of saturated fatty acids having 10 to 24 carbon atoms. Examples thereof include behenyl neopentanoate, isononyl isonanonoate, isopropyl myristate and octyl stearate.

2) Ether-esters such as fatty acid esters of ethoxylated saturated fatty alcohols.

3) Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monostearate, ethoxylated propylene glycol monostearate, glyceryl mono- and di-fatty acid esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$-$C_{30}$ alcohols.

4) Wax esters such as beeswax, spermaceti wax and tribehenin wax.

5) Sugar ester of fatty acids such as sucrose polybehenate and sucrose polycottonseedate.

Hydrocarbons which are suitable carriers include petrolatum, mineral oil, $C_{11}$-$C_{13}$ isoparaffins, and especially isohexadecane, available commercially as Permethyl 101A from Presperse Inc.

Fatty acids having from 10 to 30 carbon atoms may also be suitable as carriers. Illustrative of this category are pelargonic, lauric, myristic, palmitic, stearic, isostearic, oleic, and behenic acids.

Fatty alcohols having from 10 to 30 carbon atoms are another useful category of carrier. Illustrative of this category are stearyl alcohol, lauryl alcohol, myristyl alcohol and cetyl alcohol.

Humectants of the polyhydric alcohol-type can be employed as carriers. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. The amount of humectant may range anywhere from 0.5 to 50%, preferably between 1 and 15% by weight of the product.

Thickeners can be utilized as part of the dermatologically acceptable carriers. Typical thickeners include crosslinked acrylates (e.g. Carbopol 982®), hydrophobically-modified acrylates (e.g. Carbopol 1382®), cellulosic derivatives and natural gums. Among useful cellulosic derivatives are sodium carboxymethylcellulose, hydroxypropyl methocellulose, hydroxypropyl cellulose, hydroxyethyl cellulose, ethyl cellulose and hydroxymethyl cellulose. Natural gums may be suitable thickeners and can include guar, xanthan, *sclerotium*, carrageenan, pectin and combinations of these gums. Inorganics may also be utilized as thickeners, particularly clays such as bentonites and hectorites, fumed silicas, and silicates such as magnesium aluminum silicate (Veegum®). Amounts of the thickener may range from 0.0001 to 10%, usually from 0.001 to 1%, optimally from 0.01 to 0.5% by weight of the product.

Cosmetic products intended to be skin lighteners normally will be formulated with a skin lightening compound. Illustrative substances are placental extract, lactic acid, niacinamide, arbutin, kojic acid, ferulic acid, hydroquinone, resorcinol and derivatives including 4-substituted resorcinols and combinations thereof. Amounts of these substances may range from 0.1 to 10%, preferably from 0.5 to 2% by weight of the product.

Also included may be such materials as resveratrol, alpha-lipoic acid, ellagic acid, kinetin, retinoxytrimethylsilane (available from Clariant Corp. under the Silcare 1M-75 trademark), dehydroepiandrosterone (DHEA) and combinations thereof. Ceramides (including Ceramide 1, Ceramide 3, Ceramide 3B, Ceramide 6 and Ceramide 7) as well as pseudoceramides are useful. Amounts of these materials may range from 0.000001 to 10%, preferably from 0.0001 to 1% by weight of the composition.

Cosmetic compositions may include vitamins. Illustrative vitamins are Vitamin A (retinol), Vitamin $B_2$, Vitamin $B_3$ (niacinamide), Vitamin $B_6$, Vitamin B12, Vitamin C, Vitamin D, Vitamin E, Vitamin K and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be employed. A particularly suitable Vitamin $B_6$ derivative is Pyridoxine Palmitate. Flavonoids may also be useful, particularly glucosyl hesperidin, rutin, and soy isoflavones (including genistein, daidzein, equol, and their glucosyl derivatives) and mixtures thereof. Total amount of vitamins or flavonoids when present may range from 0.0001 to 10% by weight of the composition.

The cosmetic compositions may be formulated into a wide variety of product types that include but are not limited to solutions, suspensions, lotions, creams, gels, toners, sticks, sprays, ointments, cleansing liquid washes and solid bars, shampoos and hair conditioners, hair colorants, pastes, foams, powders, mousses, wipes, film-forming products, facial and skin masks, make-up such as foundations, eye liners, and eye shadows, and the like.

Additional sun protection may utilize organic sunscreens. They include both UVA and UVB protective ranges. Organic sunscreens will have at least one chromophoric group absorbing within the ultraviolet ranging from 290 to 400 nm. Chromophoric organic sunscreens may be divided into the following categories (with specific examples) including: p-Aminobenzoic acid, its salts and its derivatives (ethyl, isobutyl, glyceryl esters; p-dimethylaminobenzoic acid); Anthranilates (o-aminobenzoates; methyl, menthyl, phenyl, benzyl, phenylethyl, linalyl, terpinyl, and cyclohexenyl esters); Salicylates (octyl, amyl, phenyl, benzyl, menthyl, glyceryl, and dipropyleneglycol esters); Cinnamic acid derivatives (menthyl and benzyl esters, alpha-phenyl cinnamonitrile; butyl cinnamoyl pyruvate); Hydrocarbons (diphenylbutadiene, stilbene); Dibenzalacetone and benzalacetophenone; Naphtholsulfonates (sodium salts of 2-naphthol-3,6-disulfonic and of 2-naphthol-6,8-disulfonic acids); Dihydroxynaphthoic acid and its salts; o- and p-Hydroxybiphenyldisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acids; Tannic acid and its derivatives (e.g., hexaethylether); (Butyl carbityl) (6-propyl piperonyl) ether; Hydroquinone; Benzophenones (Oxybenzone, Sulisobenzone, Dioxybenzone, Benzoresorcinol, 2,2',4,4'-Tetrahydroxybenzophenone, 2,2'-Dihydroxy-4,4'-dimethoxybenzophenone, Octabenzone; 4-Isopropyldibenzoylmethane; Butylmethoxydibenzoylmethane; Etocrylene; and 4-isopropyl-dibenzoylmethane).

Particularly important sunscreens are: 2-ethylhexyl p-methoxycinnamate (available as Parsol MCX®), 4,4'-t-butyl methoxydibenzoylmethane (known commonly as Avobenzone, available as Parsol 1789®), octylsalicylate (available as Dermablock OS®), tetraphthalylidene dicamphor sulfonic acid (available as Mexoryl SX®), benzophenone-3 (Oxybenzone) and mixtures Amounts of organic sunscreen may range from 0.01 to 30%, usually from 0.5 to 15%, and often from 4 to 12% by weight of the cosmetic composition.

Surfactants suitable for use may be those which can form emulsions and/or association structures. Surfactants can be categorized as being of the anionic, nonionic, cationic, or amphoteric type. The term "surfactants" are defined herein to include materials otherwise called "emulsifiers".

Examples of surfactants which may be used in the compositions described herein include salts of $C_8$-$C_{22}$ alkyl chain compounds. Representative are sodium tallowate, sodium cocoate, sodium alkyl sulfate (e.g., sodium lauryl sulfate and sodium myristyl sulfate), sodium N-acyl sarcosinates (e.g., sodium N-lauroyl sarcosinate and sodium N-myristoyl sarcosinate), sodium dodecylbenzenesulfonate, sodium hydrogenated coconut fatty acid monoglyceride sulfate, sodium lauryl sulfoacetate and N-acyl glutamates (e.g., N-palmitoyl glutamate), N-methylacyltaurin sodium salt, N-methylacylalanine sodium salt, sodium alpha-olefin sulfonate and sodium dioctylsulfosuccinate; N-alkylaminoglycerols (e.g., N-lauryl-diamino-ethylglycerol and N-myristyldiaminoethyl glycerol), N-alkyl-N-carboxymethylammonium betaine and sodium 2-alkyl-1-hydroxyethylimidazoline betaine; polyoxyethylenealkyl ether, polyoxyethylene alkylaryl ether, polyoxyethylene lanolin alcohol, polyoxyethylene glyceryl monoaliphatic acid ester, polyoxyethylene sorbitol aliphatic acid ester, polyoxyethylene aliphatic acid ester, higher aliphatic acid glycerol ester, sorbitan aliphatic acid ester, and polyoxyethylenesorbitan aliphatic acid esters such as polyoxyethylenesorbitan monooleate and polyoxyethylene sorbitan monolaurate.

The surfactants can be used at levels from 0.1% to 97%, preferably from 2% to 75%, more preferably from 10% to 90% and most preferably from 20% to 70% by weight of the cosmetic composition.

Preservatives may be incorporated into the cosmetic compositions to protect against the growth of potentially harmful microorganisms. Suitable traditional preservatives are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are methylchloroisothiazolinone and methylisothiazolinone combinations, phenoxyethanol, methyl paraben, propyl paraben, imidazolidinyl urea, sodium dehydroacetate and benzyl alcohol. Preservatives may be employed in amounts ranging from 0.01% to 2% by weight of the cosmetic composition.

Desquamation agents may be present. Illustrative are the monocarboxylic acids. Monocarboxylic acids may be substituted or unsubstituted with a carbon chain length of up to 16. Particularly preferred carboxylic acids are the alpha-hydroxycarboxylic acids and beta-hydroxycarboxylic acids. The term "acid" is meant to include not only the free acid but also salts and $C_1$-$C_{30}$ alkyl or aryl esters thereof and lactones generated from removal of water to form cyclic or linear lactone structures. Representative acids are glycolic, lactic, malic and tartaric acids. A representative salt that is particularly preferred is ammonium lactate. Salicylic acid is representative of the beta-hydroxycarboxylic acids. Amounts of these materials when present may range from 0.01 to 15% by weight of the cosmetic composition.

Preferred desquamation agents may be selected from the group consisting of glycolic acid, lactic acid, salicylic acid, retinoic acid, retinol and mixtures thereof, and including salt forms thereof.

Colorants may either be dyes or pigments. A distinction is usually made between a pigment, which is insoluble in its vehicle (resulting in a suspension), and a dye, which either is itself a liquid or is soluble in its vehicle (resulting in a solution). A colorant can act as either a pigment or a dye depending on the vehicle involved. In some cases, a pigment can be manufactured from a dye by precipitating a soluble dye with a metallic salt. The resulting pigment is called a lake pigment.

Among the more common dyes are Alizarin, Azophloxin, Chrysoidin, Congo Red, Fuchsin acid, Gentian violet, Janus green, Methyl Red, Naphthol Green, Naphthol Yellow, Rose Bengal, Sudan II, Titan Yellow and combinations thereof. Amongst pigments, titanium dioxide and aluminum lakes (aluminum salts of dyes) are most common. Amounts of the colorant may, according to the type of cosmetic product (lipstick, foundation, hair dye, etc.) range from 0.000001 to 10%, usually from 0.01 to 5% by weight of the cosmetic composition.

The sun protection factor (SPF rating) has been used to qualitatively describe differences in protective efficacy. SPF is a measure of the fraction of sunburn-producing UV rays that reach the skin. For example, "SPF 15" means that $\frac{1}{15}$th of the burning radiation will reach the skin, assuming sunscreen is applied evenly at a thick dosage of 2 milligrams per square centimeter ($mg/cm^2$). A user can determine the effectiveness of a sunscreen by multiplying the SPF factor by the length of time it takes for him or her to suffer a burn without sunscreen. Thus, if a person develops a sunburn in 10 minutes when not wearing a sunscreen, the same person in the same intensity of sunlight will avoid sunburn for 150 minutes if wearing a sunscreen with an SPF of 15.

Besides an in vivo measurement, SPF can also be measured in vitro with the help of a specially designed spectrometer. In this case, the actual transmittance of the sunscreen is measured, along with the degradation of the product due to being exposed to sunlight. Transmittance of the sunscreen must be measured over all wavelengths in sunlight's UVB-UVA range (290-400 nm), along with a table of how effective various wavelengths are in causing sunburn (the erythema/action spectrum) and the standard intensity spectrum of sunlight. Evaluations of SPF in the Examples which follow report results by the in vitro method.

Except in the examples, or where otherwise explicitly indicated, all numbers in this description indicating amounts of material or conditions of reaction, physical properties of materials and/or use are to be understood as modified by the word "about." All amounts are by weight of the compositions, unless otherwise specified.

It should be noted that in specifying any range of concentration or amount, any particular upper concentration can be associated with any particular lower concentration or amount.

For the avoidance of doubt, the word "comprising" is intended to mean "including" but not necessarily "consisting of" or "composed of." In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

"Product" as used herein, is meant to include a formulated personal care or cleansing composition for topical application to skin or hair of mammals, especially humans or for deposition onto textiles via laundering.

Example I

A series of experiments were run focused on the coating of micronized zinc oxide with polyhydroxystearic acid (PHSA) by a variety of coating techniques. Comparisons are made to the known oily dispersant route.

High Speed Dry Milling and Coating Method

Zinc oxide was added to tank with high speed mixer and mixed for a few minutes to de-agglomerate. The coating polyhydroxystearic acid was sprayed onto the zinc oxide while the latter was being mixed at high speed. Thereafter, mixing was continued for at least 15 minutes to totally disperse the coating (PHSA). Suitable high speed mixers include the Jet mill, Lodige mixer, and Baker Perkins equipment. Amounts and source of the materials are reported in the Table below.

| Trade Name | Ingredient (INCI) | Supplier | % |
|---|---|---|---|
| Dispersun DSP-OL 100 | Polyhydroxystearic Acid (PHA) | Innospec | 4.0 |
| Zinc Oxide | Zinc Oxide | Next Step Lab | 96.0 |

Liquid or Supercritical Carbon Dioxide Method

Zinc oxide (ZnO) was added to a high pressure tank equipped with a mixer (magnetic). Supercritical carbon dioxide ($CO_2$) was added to the coating PHA and the combination mixed before injection into the high pressure tank containing ZnO and where $CO_2$ was a liquid. The mixture of ZnO and $CO_2$/PHSA was mixed for approximately 10 minutes. Thereafter, contents of the tank were discharged into a container where carbon dioxide was allowed to sublime and PHSA coated ZnO powder remained behind. Amounts and source of the materials are reported in the Table below.

| Trade Name | Ingredient (INCI) | Supplier | % |
|---|---|---|---|
| Dispersun DSP-OL 100 | Polyhydroxystearic Acid (PHA) | Innospec | 4.0 |
| Zinc Oxide | Zinc Oxide | Next Step Lab | 96.0 |

Slurry Coating Method

Polyhydroxystearic Acid (PHSA) was added to Isododecane and mixed to dissolve the coating (PHSA). Zinc oxide was added with high shear agitation by a Silverson (L5M-A) mixer and mixed for 30 minutes. The resultant slurry was poured into a drying tray and dried for 24 hours at 70° C. to remove Isododecane. Amounts and source of the materials are reported in the Table below.

| Trade Name | Ingredient (INCI) | Supplier | % |
|---|---|---|---|
| Purolan IDD | Isododecane | Lanxess | 50.0 |
| Dispersun DSP-OL 100 | Polyhydroxystearic Acid (PHSA) | Innospec | 2.0 |
| Zinc Oxide | Zinc Oxide | Next Step Lab | 48.0 |

Dispersions for all 3 Coatings Above (Slurry, Liquid $CO_2$, Dry Milling)

| | |
|---|---|
| Tricaprylin | 50.0 |
| PHSA Coated ZnO | 50.0 |

Dispersion (Per Supplier of PHA)

| | |
|---|---|
| Tricaprylin | 50.0 |
| PHSA | 2.0 |
| ZnO | 48.0 |

Example II

Comparison results are reported in the Table below. These compare SPF and viscosity of dispersions of pre-coated PHSA onto zinc oxide with subsequent dispersal in oil versus post-coating of an oil/PHSA slurry onto zinc oxide.

| Coating method | Processing Temp | Viscosity | SPF** |
|---|---|---|---|
| High speed dry milling (1) | 25° C.-60° C.* | 95-100 cps | 26-28 |
| Supercritical $CO_2$ (2) | 10° C.-25° C. | 95-100 cps | 26-28 |
| Slurry Coating (3) | 25° C.-50° C.* | 95-100 cps | 26-28 |
| Dispersion per supplier of PHA (4) | 25° C.-60° C.* | 258-275 cps | 13-14 |

*Temperature rise due to shear
**10% Zinc Oxide

Pre-coating (methods 1-3) zinc oxide with PHSA followed by dispersing in an oil gave a much lower viscosity and doubled SPF. The traditional preparation (method 4) of an oil/PHSA dispersion being added to the zinc oxide was seen to be significantly inferior regarding viscosity and SPF.

Formula Tested for SPF

| Phase | Ingredient | 1 | 4 |
|---|---|---|---|
| A | Tricaprylin ZnO Dispersion (pre-coated with PHSA) | 21.0* | — |
| | Tricaprylin ZnO Dispersion (per PHSA supplier) | — | 21.0* |
| A | Tricaprylin | 22.7 | 22.7 |
| A | Polyglyceryl-3 polyricinoleate | 2.0 | 2.0 |
| A | Isododecane | 7.8 | 7.8 |
| B | Quaternium-90 Bentonite | 2.6 | 2.6 |
| C | Polyglyceryl-3 diisostearate | 1.3 | 1.3 |
| C | Cetyl PEG/PPG-10/1 Dimethicone | 1.3 | 1.3 |
| D | Water | 39.5 | 39.5 |
| D | Magnesium Sulphate | 1.5 | 1.5 |
| D | Potassium Sorbate | 0.3 | 0.3 |
| | | 100.0 | 100.0 |

*10% Zinc Oxide

Example III

PHSA coated ZnO can be used to make sunscreen formulations of various types but not limited to: W/O; O/W; pickering emulsions; anhydrous; alcohol-based suspension. Illustrative cosmetic product formulations are described below.

W/O Emulsion

| Phase | Ingredient | 1 | 2 | 3 | 4 | 5 |
|---|---|---|---|---|---|---|
| A | PHSA Coated ZnO | 30.0 | 1.0 | 5.0 | 10.0 | 20.0 |
| A | Tricaprylin | 24.8 | 32.7 | 29.8 | 28.8 | 25.3 |
| A | Isododecane | 7.8 | 8.9 | 7.8 | 7.8 | 7.8 |
| B | Quaternium-90 Bentonite | 2.6 | 2.6 | 2.6 | 2.6 | 2.6 |
|   | Propylene Carbonate | 1.0 | 1.0 | 1.0 | 1.0 | 1.0 |
| C | Cetyl PEG/PPG-10/1 Dimethicone | 2.0 | 2.0 | 2.0 | 2.0 | 2.0 |
| D | Water | 30.0 | 50.0 | 50.0 | 46.0 | 39.5 |
| D | Magnesium Sulphate | 1.5 | 1.5 | 1.5 | 1.5 | 1.5 |
| D | Potassium Sorbate | 0.3 | 0.3 | 0.3 | 0.3 | 0.3 |
|   |   | 100.0 | 100.0 | 100.0 | 100.0 | 100.0 |

O/W Emulsion

| Phase | Ingredient | 1 | 2 | 3 |
|---|---|---|---|---|
| A | Water | 59.3 | 54.3 | 49.3 |
| A | Glycerin | 3.0 | 3.0 | 3.0 |
| A | Potassium Sorbate | 0.30 | 0.30 | 0.30 |
| B | PHSA Coated ZnO | 5.0 | 10.0 | 15.0 |
| B | Tricaprylin | 20.0 | 20.0 | 20.0 |
| B | Isododecane | 7.8 | 7.8 | 7.8 |
| B | Arlacel ® 165 | 2.6 | 2.6 | 2.6 |
| C | Aristoflex AVC ® | 1.0 | 1.0 | 1.0 |
| D | Phenoxyethanol | 1.0 | 1.0 | 1.0 |
|   |   | 100.0 | 100.0 | 100.0 |

Example IV

A series of experiments were run focused on the coating of micronized titanium dioxide with polyhydroxystearic acid (PHSA) by a variety of coating techniques. Comparisons are made to the known oily dispersant route.

Dispersions for all Three Coating Methods Above (Slurry, Liquid $CO_2$, Dry Milling)

| Tricaprylin | 50.0 |
|---|---|
| PHSA Coated TiO2 | 50.0 |

Dispersion (per supplier of PHA)

| Tricaprylin | 50.0 |
|---|---|
| PHSA | 2.0 |
| $TiO_2$ | 48.0 |

Formula Tested for SPF

| Phase | Ingredient | 1 | 2 |
|---|---|---|---|
| A | Tricaprylin $TiO_2$ Dispersion (Pre-coated with PHSA) | 10.5* | — |
|   | Tricaprylin $TiO_2$ Dispersion (Per PHSA supplier) | — | 10.5* |
| A | Tricaprylin | 33.2 | 33.2 |
| A | Polyglyceryl-3 polyricinoleate | 2.0 | 2.0 |
| A | Isododecane | 7.8 | 7.8 |
| B | Quaternium-90 Bentonite | 2.6 | 2.6 |
| C | Polyglyceryl-3 diisostearate | 1.3 | 1.3 |
| C | Cetyl PEG/PPG-10/1 Dimethicone | 1.3 | 1.3 |
| D | Water | 39.5 | 39.5 |
| D | Magnesium Sulphate | 1.5 | 1.5 |
| D | Potassium Sorbate | 0.3 | 0.3 |
|   |   | 100.0 | 100.0 |

*5% $TiO_2$

Example V

Comparison results with titanium dioxide are reported in the Table below. These compare SPF and viscosity of dispersions of pre-coated PHSA onto titanium dioxide with subsequent dispersal in oil versus post-coating of an oil/PHSA slurry onto titanium dioxide.

Dispersion vs Coating Results

| Coating method | Processing Temp | Viscosity | SPF** |
|---|---|---|---|
| High speed dry milling (1) | 25° C.-60° C.* | 86-90 cps | 35-40 |
| Supercritical $CO_2$ (2) | 10° C.-25° C. | 86-90 cps | 35-40 |
| Slurry Coating (3) | 25° C.-50° C.* | 86-90 cps | 35-40 |
| Dispersion per supplier of PHA (4) | 25° C.-60° C.* | 450-475 cps | 20-25 |

*Temperature rise due to shear
**5% Titanium Dioxide tested using in-vitro method Pre-coating (methods 1-3) titanium dioxide with PHSA followed by dispersing in an oil gave a much lower viscosity and doubled SPF. The traditional preparation (method 4) of an oil/PHA dispersion being added to the titanium dioxide was seen to be significantly inferior regarding viscosity and SPF.

Example VI

PHSA coated titanium dioxide can be used to make sunscreen formulations of various types but not limited to: W/O; O/W; pickering emulsions; anhydrous; alcohol-based suspension. Illustrative cosmetic product formulations are described below.

W/O Emulsion

| Phase | Ingredient | 1 | 2 | 3 | 4 | 5 |
|---|---|---|---|---|---|---|
| A | PHSA Coated $TiO_2$ | 30.0 | 1.0 | 5.0 | 10.0 | 20.0 |
| A | Tricaprylin | 24.8 | 32.7 | 29.8 | 28.8 | 25.3 |
| A | Isododecane | 7.8 | 8.9 | 7.8 | 7.8 | 7.8 |
| B | Quaternium-90 Bentonite | 2.6 | 2.6 | 2.6 | 2.6 | 2.6 |
|   | Propylene Carbonate | 1.0 | 1.0 | 1.0 | 1.0 | 1.0 |
| C | Cetyl PEG/PPG-10/1 Dimethicone | 2.0 | 2.0 | 2.0 | 2.0 | 2.0 |
| D | Water | 30.0 | 50.0 | 50.0 | 46.0 | 39.5 |
| D | Magnesium Sulphate | 1.5 | 1.5 | 1.5 | 1.5 | 1.5 |
| D | Potassium Sorbate | 0.3 | 0.3 | 0.3 | 0.3 | 0.3 |
|   |   | 100.0 | 100.0 | 100.0 | 100.0 | 100.0 |

O/W Emulsion

| Phase | Ingredient | 1 | 2 | 3 |
|---|---|---|---|---|
| A | Water | 59.3 | 54.3 | 49.3 |
| A | Glycerin | 3.0 | 3.0 | 3.0 |
| A | Potassium Sorbate | 0.30 | 0.30 | 0.30 |
| B | PHSA Coated Titanium Dioxide | 5.0 | 10.0 | 15.0 |

-continued

| Phase | Ingredient | 1 | 2 | 3 |
|---|---|---|---|---|
| B | Tricaprylin | 20.0 | 20.0 | 20.0 |
| B | Isododecane | 7.8 | 7.8 | 7.8 |
| B | Arlacel ® 165 | 2.6 | 2.6 | 2.6 |
| C | Aristoflex AVC ® | 1.0 | 1.0 | 1.0 |
| D | Phenoxyethanol | 1.0 | 1.0 | 1.0 |
|   |   | 100.0 | 100.0 | 100.0 |

O/W Emulsion

| Phase | Ingredient | 1 | 2 | 3 |
|---|---|---|---|---|
| A | Water | 59.3 | 54.3 | 49.3 |
| A | Glycerin | 3.0 | 3.0 | 3.0 |
| A | Potassium Sorbate | 0.30 | 0.30 | 0.30 |
| B | PHSA Coated Titanium Dioxide | 5.0 | 10.0 | 15.0 |
| B | Tricaprylin | 15.0 | 15.0 | 15.0 |
| B | Benzophenone-3 | 3.0 | 3.0 | 3.0 |
| B | Isododecane | 7.8 | 7.8 | 7.8 |
| B | Arlacel ® 165 | 2.6 | 2.6 | 2.6 |
| C | Aristoflex AVC ® | 1.0 | 1.0 | 1.0 |
| D | Phenoxyethanol | 1.0 | 1.0 | 1.0 |
|   |   | 100.0 | 100.0 | 100.0 |

Example VI

Zeta Potential measurements and methodology are discussed under this Example. Measurements were taken using a ZetaProbe Analyzer™ commercially available from the Colloidal Dynamics Company of Ponte Vedra Beach, Fla. A 10% zinc oxide slurry in n-dodecane was the standard level analyzed and represents conditions for Zeta Potential values described by the claims. Before initial measuring, the system was calibrated. The sample stirring paddle operated at 170 rpm and a 5 minute wait period was used to stabilize the sample. Three scans were averaged per sample. The results are recorded in millivolts (mV) at the 1 minute mark post the 5 minute stabilization wait period.

Procedures employed to obtain the samples that were measured are outlined below.

Zeta Potential Samples

| Sample: | A | B | C |
|---|---|---|---|
| Dodecane | 90.0% | 90.0% | 89.4% |
| Zinc Oxide (Zoco) | 10.0% | — | 10.0% |
| PHSA | — | — | 0.6% |
| Super Zinc Natural* | — | 10.0% | — |

*Super Zinc Natural - 94.0% Zinc Oxide/6% PHA

Procedure for Sample A:
1. Weighed Dodecane and added to beaker
2. Placed on homogenizer—2500 RPM
3. Added Zinc Oxide to dodecane while homogenizing
4. Allowed to mix for 30 minutes at 2500 RPM Procedure for Sample B:
1. Weighed Dodecane and added to beaker
2. Placed on homogenizer—2500 RPM
3. Added Super Zinc Natural to dodecane while homogenizing
4. Added Zinc Oxide to dodecane/PHSA mixture while homogenizing Procedure for Sample C:
1. Weighed Dodecane and added to beaker
2. Placed on homogenizer—2500 RPM
3. Added PHSA to dodecane while homogenizing
4. Added Zinc Oxide to dodecane/PHSA mixture while homogenizing
5. Allowed to mix for 30 minutes at 2500 RPM Sample A represents a control experiment without any PHSA. Sample B is illustrative of the present invention wherein PHSA was deposited onto the zinc oxide and carrier vehicle evaporated to form a powdered zinc oxide/PHSA before the powder was slurried (e.g. with dodecane) into a product.

Zeta Potential has been used to gain information on the surface charge of coating treated metal oxide particles. We have found a correlation between surface charge (mV) and the sun protective factor (SPF). The larger the charge, the higher the SPF protection. SPF improvement has been reported under Example II with samples similar to Sample B (the present invention). Control Sample A (pure uncoated zinc particles) and the art described Sample C (slurry delivered PHSA) displayed significantly smaller Zeta Potential values than did Sample B. Note the values in the Table below.

| Sample: | A | B | C |
|---|---|---|---|
| Zeta Potential (mv) | 0.47 | 2.49 | 0.69 |

While the present compositions and methods have been described with reference to the specific variations thereof, it should be understood by those skilled in the art that various changes may be made and equivalents may be substituted without departing from the true spirit and scope of the compositions and methods described herein. In addition, many modifications may be made to adapt a particular situation, material, composition of matter, process, process step or steps, to the objective, spirit and scope of the compounds and methods described herein. All patents and publications cited above are hereby incorporated by reference.

What is claimed is:

1. An ultraviolet radiation sun protective composition, comprising: micronized metal oxide inorganic particles selected from the group consisting of zinc oxide, titanium oxide and mixtures thereof, the inorganic particles being coated with polyhydroxystearic acid, the coated particles measured at a 10% loading in dodecane and 1 minute elapsed time having a Zeta Potential ranging from 2 to 10 mv, the amounts of the polyhydroxystearic acid and the inorganic particles being in a relative weight ratio of 1:100 to 1:10, and the coated particles being free of an oily dispersant.

2. The composition according to claim 1, wherein:
the Zeta Potential ranges from 2 to 5 mv.

3. The composition according to claim 1, wherein:
the coated particles are characterized when dispersed in tricaprylin at a 1:1 weight ratio as having a Brookfield Viscosity measured at 23-28° C., 20 rpm with spindle 4, ranging from 20 to 200 cps.

4. The composition according to claim 1, wherein:
the composition is formed in an oily dispersant free process selected from the group consisting of (1) high speed milling, (2) supercritical carbon dioxide processing and (3) solvent slurry application with subsequent solvent removal.

5. The composition according to claim 1, wherein:
the polyhydroxystearic acid and the inorganic particles are in a relative weight ratio of 1:50 to 1:20.

6. The composition according to claim 1, wherein:

the inorganic particles have primary particle size ranging from 5 to 500 nm.

7. A cosmetic product, comprising:

(i) an ultraviolet radiation sun protective composition comprising micronized metal oxide inorganic particles selected from the group consisting of zinc oxide, titanium oxide and mixtures thereof, the inorganic particles being coated with poly[$C_8$-$C_{20}$ hydroxycarboxylic acid], the coated particles measured at a 10% loading in dodecane and 1 minute elapsed time having a Zeta Potential ranging from 2 to 10 mv, the amounts of the poly[$C_8$-$C_{20}$ hydroxycarboxylic acid] and the inorganic particles being in a relative weight ratio of 1:100 to 1:10; and (ii) a dermatologically acceptable carrier supporting the ultraviolet radiation sun protective composition, the composition being present in the carrier in a relative weight ratio of 1:100 to 1:5.

8. The product according to claim 7, wherein:

the carrier is selected from the group consisting of water, emollients, fatty acids, fatty alcohols, humectants, thickeners and mixtures thereof.

9. The product according to claim 7, wherein:

the coated ultraviolet sun protective composition and the carrier are present in a relative weight ratio of 1:100 to 1:10.

10. The product according to claim 7, wherein:

the carrier is present in an amount from 1 to 99.9% by weight of the cosmetic product.

11. The product according to claim 7, further comprising:

one or more organic sunscreens selected from the group consisting of 2-ethylhexyl p-methoxycinnamate, 4,4'-t-butyl methoxydibenzoylmethane, octylsalicylate, tetraphthalylidene dicamphor sulfonic acid, benzophenone-3 and mixtures thereof.

12. The composition according to claim 7, wherein:

the poly[$C_8$-$C_{20}$ hydroxycarboxylic acid] is selected from the group consisting of polyhydroxystearic acid, polyricinoleic acid and mixtures thereof.

13. The composition according to claim 7, wherein:

the poly [$C_8$-$C_{20}$ hydroxycarboxlic acid] is polyhydroxystearic acid.

14. The composition according to claim 1, wherein the coated particles are in powdered form.

15. The product according to claim 7, wherein the coated particles are in powdered form.

\* \* \* \* \*